(12) United States Patent
Auersperg et al.

(10) Patent No.: US 7,407,762 B2
(45) Date of Patent: Aug. 5, 2008

(54) DIAGNOSIS OF GYNECOLOGICAL NEOPLASMS BY DETECTING THE LEVELS OF OVIDUCT-SPECIFIC GLYCOPROTEIN

(75) Inventors: Nelly Auersperg, Vancouver (CA); Michelle Woo, Richmond (CA); C. Blake Gilks, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 0 days.

(21) Appl. No.: 10/548,580

(22) PCT Filed: Mar. 11, 2004

(86) PCT No.: PCT/CA2004/000367

§ 371 (c)(1),
(2), (4) Date: Jul. 17, 2006

(87) PCT Pub. No.: WO2004/102200

PCT Pub. Date: Nov. 25, 2004

(65) Prior Publication Data

US 2007/0026399 A1 Feb. 1, 2007

Related U.S. Application Data

(60) Provisional application No. 60/453,207, filed on Mar. 11, 2003.

(51) Int. Cl.
*G01N 33/53* (2006.01)
(52) U.S. Cl. ............................................. 435/7.1
(58) Field of Classification Search .................. None
See application file for complete search history.

(56) References Cited

FOREIGN PATENT DOCUMENTS

| WO | WO 02/086443 | 10/2002 |
| WO | WO02/086443 | * 10/2002 |

OTHER PUBLICATIONS

Tockman et al (Cancer Res., 1992, 52:2711s-2718s).*
O'Day-Bowman et al (Biology of Reproduction, Jan. 1996, 54:60-69).*
Ogawa et al (American Journal of Pathology, Oct. 1999, 155(4):1047-1050).*
Rustin et al (Annals of Oncology, Apr. 1996, 7:361-364).*
Klug et al (Cancer Research, Mar. 1984, 44:1048-1053).*
Arias et al. (Arias EB et al., Biol. Reprod. 51, pp. 685-694 (1994)).*
Klug et al (Cancer Reasearch, Mar. 1984, 44: 1048-1053).*
Rapisarda, John et al., Immunological characterization and immunocytochemical localization of an oviduct-specific glycoprotein in the human, Journal of Clinical Endocrinology and Metabolism, vol. 76, No. 6, 1993, pp. 1483-1488.
Miyoshi, Ichiro et al., Mouse transgenic for murine oviduct-specific glycoprotein promoter-driven simian virus 40 large T-antigen: Tumor formation and its hormonal regulation, Molecular Reproduction and Development, vol. 63, No. 2, Oct. 2002, pp. 168-176.
Lagow, Errin et al., Mammalian reproductive tract mucins, Human Reproduction Update, vol. 5, No. 4, Jul. 1999, pp. 280-292.
Buhi, William C., Characterization and biological roles of oviduct-specific, oestrogen-dependent glycoprotein, Reproduction, vol. 123, No. 3, Mar. 2002, pp. 355-362.
Mazurek, A et al., Clinical tumour markers in ovarian cancer, European Journal of Cancer Prevention: The Official Journal of the European Cancer Prevention Organisation (ECP), Feb. 1998, vol. 7, No. 1, Feb. 1998, pp. 23-25.
Bast, R.C. et al., CA 125: The past and the future, International Journal of Biological Markers, Wichtig Editore, Milan, IT, vol. 13, No. 4, Oct. 1998, pp. 179-187.
Hellstrom, Ingegerd et al., The HE4 (WFDC2) protein is a biomarker for ovarian carcinoma, Cancer Research, vol. 63, No. 13, Jul. 1, 2003, pp. 3695-3700.
Woo, Michelle M.M. et al., Oviductal glycoprotein (OGP), a new differentiation-based indicator of ovarian and endometrial (pre)neoplastic changes, Proceedings of the American Association for Cancer Research Annual Meeting, vol. 44, Jul. 2003, p. 1343.
Woo, Michelle M.M. et al., Oviductal glycoprotein, a new differentiation-based indicator present in early ovarian epithelial neoplasia and cortical inclusion cysts, Gynecologic Oncology, vol. 93, No. 2, May 2004, pp. 315-319.

* cited by examiner

*Primary Examiner*—Misook Yu
*Assistant Examiner*—Sean Aeder
(74) *Attorney, Agent, or Firm*—Bereskin & Parr; Micheline Gravelle (57) ABSTRACT

The present invention provides a method for detecting cancer in a patient. A sample from the patient is provided, and the level of oviduct-specific glycoprotein (OGP) in the sample is determined and compared to a control sample. Increased levels of OGP in the sample as compared to the control indicates that the patient has cancer. In one aspect, the cancer is a gynecological cancer, such as ovarian cancer. Kits for conducting the methods of the invention are also provided.

12 Claims, 1 Drawing Sheet

Figure 1

SEQUENCE LISTING

```
<160> NUMBER OF SEQ ID NOS: 1

<210> SEQ ID NO 1
<211> LENGTH: 678
<212> TYPE: PRT
<213> ORGANISM: Homo sapiens

<400> SEQUENCE: 1

Met Trp Lys Leu Leu Leu Trp Val Gly Leu Val Leu Val Leu Lys His
1               5                   10                  15

His Asp Gly Ala Ala His Lys Leu Val Cys Tyr Phe Thr Asn Trp Ala
            20                  25                  30

His Ser Arg Pro Gly Pro Ala Ser Ile Leu Pro His Asp Leu Asp Pro
```

-continued

```
                35                  40                  45
Phe Leu Cys Thr His Leu Ile Phe Ala Phe Ala Ser Met Asn Asn Asn
 50                  55                  60

Gln Ile Val Ala Lys Asp Leu Gln Asp Glu Lys Ile Leu Tyr Pro Glu
 65                  70                  75                  80

Phe Asn Lys Leu Lys Glu Arg Asn Arg Glu Leu Lys Thr Leu Leu Ser
                 85                  90                  95

Ile Gly Gly Trp Asn Phe Gly Thr Ser Arg Phe Thr Thr Met Leu Ser
                100                 105                 110

Thr Phe Ala Asn Arg Glu Lys Phe Ile Ala Ser Val Ile Ser Leu Leu
                115                 120                 125

Arg Thr His Asp Phe Asp Gly Leu Asp Leu Phe Phe Leu Tyr Pro Gly
                130                 135                 140

Leu Arg Gly Ser Pro Met His Asp Arg Trp Thr Phe Leu Phe Leu Ile
145                 150                 155                 160

Glu Glu Leu Leu Phe Ala Phe Arg Lys Glu Ala Leu Leu Thr Met Arg
                165                 170                 175

Pro Arg Leu Leu Leu Ser Ala Ala Val Ser Gly Val Pro His Ile Val
                180                 185                 190

Gln Thr Ser Tyr Asp Val Arg Phe Leu Gly Arg Leu Leu Asp Phe Ile
                195                 200                 205

Asn Val Leu Ser Tyr Asp Leu His Gly Ser Trp Glu Arg Phe Thr Gly
                210                 215                 220

His Asn Ser Pro Leu Phe Ser Leu Pro Glu Asp Pro Lys Ser Ser Ala
225                 230                 235                 240

Tyr Ala Met Asn Tyr Trp Arg Lys Leu Gly Ala Pro Ser Glu Lys Leu
                245                 250                 255

Ile Met Gly Ile Pro Thr Tyr Gly Arg Thr Phe Arg Leu Leu Lys Ala
                260                 265                 270

Ser Lys Asn Gly Leu Gln Ala Arg Ala Ile Gly Pro Ala Ser Pro Gly
                275                 280                 285

Lys Tyr Thr Lys Gln Glu Gly Phe Leu Ala Tyr Phe Glu Ile Cys Ser
                290                 295                 300

Phe Val Trp Gly Ala Lys Lys His Trp Ile Asp Tyr Gln Tyr Val Pro
305                 310                 315                 320

Tyr Ala Asn Lys Gly Lys Glu Trp Val Gly Tyr Asp Asn Ala Ile Ser
                325                 330                 335

Phe Ser Tyr Lys Ala Trp Phe Ile Arg Arg Glu His Phe Gly Gly Ala
                340                 345                 350

Met Val Trp Thr Leu Asp Met Asp Asp Val Arg Gly Thr Phe Cys Gly
                355                 360                 365

Thr Gly Pro Phe Pro Leu Val Tyr Val Leu Asn Asp Ile Leu Val Arg
                370                 375                 380

Ala Glu Phe Ser Ser Thr Ser Leu Pro Gln Phe Trp Leu Ser Ser Ala
385                 390                 395                 400

Val Asn Ser Ser Thr Asp Pro Glu Arg Leu Ala Val Thr Thr Ala
                405                 410                 415

Trp Thr Thr Asp Ser Lys Ile Leu Pro Pro Gly Gly Glu Ala Gly Val
                420                 425                 430

Thr Glu Ile His Gly Lys Cys Glu Asn Met Thr Ile Thr Pro Arg Gly
                435                 440                 445

Thr Thr Val Thr Pro Thr Lys Glu Thr Val Ser Leu Gly Lys His Thr
                450                 455                 460
```

-continued

```
Val Ala Leu Gly Glu Lys Thr Glu Ile Thr Gly Ala Met Thr Met Thr
465                 470                 475                 480

Ser Val Gly His Gln Ser Met Thr Pro Gly Glu Lys Ala Leu Thr Pro
                485                 490                 495

Val Gly His Gln Ser Val Thr Thr Gly Gln Lys Thr Leu Thr Ser Val
            500                 505                 510

Gly Tyr Gln Ser Val Thr Pro Gly Glu Lys Thr Leu Thr Pro Val Gly
        515                 520                 525

His Gln Ser Val Thr Pro Val Ser His Gln Ser Val Ser Pro Gly Gly
    530                 535                 540

Thr Thr Met Thr Pro Val His Phe Gln Thr Glu Thr Leu Arg Gln Asn
545                 550                 555                 560

Thr Val Ala Pro Arg Arg Lys Ala Val Ala Arg Glu Lys Val Thr Val
                565                 570                 575

Pro Ser Arg Asn Ile Ser Val Thr Pro Glu Gly Gln Thr Met Pro Leu
            580                 585                 590

Arg Gly Glu Asn Leu Thr Ser Glu Val Gly Thr His Pro Arg Met Gly
        595                 600                 605

Asn Leu Gly Leu Gln Met Glu Ala Glu Asn Arg Met Met Leu Ser Ser
    610                 615                 620

Ser Pro Val Ile Gln Leu Pro Glu Gln Thr Pro Leu Ala Phe Asp Asn
625                 630                 635                 640

Arg Phe Val Pro Ile Tyr Gly Asn His Ser Ser Val Asn Ser Val Thr
                645                 650                 655

Pro Gln Thr Ser Pro Leu Ser Leu Lys Lys Glu Ile Pro Glu Asn Ser
            660                 665                 670

Ala Val Asp Glu Glu Ala
            675
```

DIAGNOSIS OF GYNECOLOGICAL NEOPLASMS BY DETECTING THE LEVELS OF OVIDUCT-SPECIFIC GLYCOPROTEIN

FIELD OF THE INVENTION

The invention relates to methods for detecting gynecological neoplasms. The method involves detecting levels of oviduct-specific glycoprotein (OGP).

BACKGROUND OF THE INVENTION

In developed countries, epithelial ovarian carcinoma (EOC) remains the most lethal gynecologic malignancy and the fourth or fifth most common cause of death from all cancers in women. To date, however, there are no means for early detection of ovarian cancer, nor is there a definitive system for accurately determining the classification of these tumors. The fatality of this disease stems from the frequent lack of symptoms until the tumors have disseminated beyond the ovary. As a result, the five-year survival rate of women with ovarian cancer remains a low and discouraging 40-50% [American Cancer Society, 2003; Jemal, A. et al., 2003]. If the tumor is still confined to the ovary, the chances of survival increase to a substantial 80-90%. Despite the clinical importance of EOC, the early progression of the disease is still poorly understood.

Over 85% of ovarian neoplasms, including carcinomas, cystadenomas and borderline tumors are thought to arise from the ovarian surface epithelium (OSE) or its derivatives, epithelial crypts and inclusion cysts [Scully, R E, 2000; Auersperg, N. et al., 2001]. The OSE is a simple mesothelium covering the ovary. As OSE progresses to malignancy, it acquires characteristics of the more complex Mullerian duct-derived epithelia of the oviduct, endometrium, or endocervix [Scully, R. E. et al., 1998]. Like these epithelia; differentiated ovarian carcinomas form glandular and papillary structures and acquire more highly specialized and complex epithelial characteristics, including E-cadherin [Maines-Bandiera, S. L. and Auersperg, N., 1997; Sundfeldt, K. et al., 1997; Davies, B. R. et al., 1998] and CA-125 [Bast, R. C. Jr. et al., 1998]. Thus, in contrast to other tissues where carcinogenesis is accompanied by a loss in differentiation, malignant OSE acquires a more highly differentiated epithelial phenotype, along the lines of Mullerian duct derivatives. These changes may reflect the common embryonic origin from which the OSE and Mullerian duct epithelia are derived, the urogenital coelomic epithelium [Scully, R. E., 2000].

Mullerian differentiation is so frequent in ovarian neoplasms that it serves as the basis for the classification of these tumors [American Cancer Society, 2003]. The most common type of ovarian cancer are the serous carcinomas which resemble oviductal epithelium. Except for CA125, there are at present no molecular markers that characterize tubal differentiation and serve as predictive or diagnostic markers in ovarian cancer [Bast, R. C. Jr. et al., 1998; Hellstrom, I. et al., 2003; Mazurek, A. et al., 1998].

OGP, oviduct-specific glycoprotein, is a specific tubal differentiation marker [Rapisarda, J. J. et al., 1993; Arias, E. B. et al., 1994; Lesse, H. J. et al., 2001]. OGP is normally secreted specifically and exclusively by the secretory epithelial cells of the oviduct, under estrogen dominance [Arias, E. B. et al., 1994; O'Day-Bowman, M. B. et al., 1995; Jaffe, R. C. et al., 1996]. It is more specific than CA125, which is normally also produced by the endometrium and endocervix [Kabawat, S. E. et al., 1983]. The human genome contains a single copy of the OGP gene located on chromosome 1p13 [Lapensee, L. et al., 1997]. It is a heavily glycosylated protein, like CA125, with a molecular weight of 110- to 130-kDa and is believed to play a role in fertilization and early embryonic development [Verhage, H. G. et al., 1988; Boice, M. L. et al., 1990; Boatman, D. E. and Magnoni, G. E., 1995; O'Day-Bowman, M. B. et al., 1996; Schmidt, A. et al., 1997].

SUMMARY OF THE INVENTION

The present inventors have determined that oviduct-specific glycoprotein (OGP) is a marker expressed during the aberrant Mullerian epithelial differentiation of ovarian neoplasms.

Accordingly, in one embodiment, the present invention provides a method for detecting cancer in a patient comprising:
(a) providing a sample from the patient;
(b) detecting the level of OGP in the sample; and
(c) comparing the level of OGP in the sample to a control sample, wherein increased levels of OGP as compared to the control indicates that the patient has cancer.

In another embodiment, the present invention provides a method for monitoring the progression of cancer in a patient, comprising:
(a) providing a sample from a patient;
(b) determining the level of OGP in the sample;
(c) repeating steps (a) and (b) at a later point in time and comparing the result of step (b) with the result of step (c) wherein a difference in the level of OGP expression is indicative of the progression of the cancer in the patient.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawing in which.

DETAILED DESCRIPTION OF THE INVENTION

Immunohistochemical analysis for OGP was performed on 389 ovarian tumors and 19 normal ovaries, as well as 433 cases representing 45 normal tissues and 51 benign and malignant tumor types from 37 different tissues.

OGP was absent in ovarian surface epithelium (OSE) but present in $28/31$ epithelial inclusion cysts, $13/14$ (93%) serous cystadenomas and $46/65$ (71%) serous borderline tumors. Of 183 serous, adenocarcinomas, 26 (14%) were positive for OGP, including $5/8$ (63%) grade I, $7/41$ (17%) grade II and $14/134$ (10%) grade III carcinomas. OGP was found in $7/14$ (50%) borderline and $9/15$ (60%) malignant mucinous ovarian tumors and in 10/39 (26%) endometriold adenocarcinomas. The localization of OGP in the lumen of glandular structures suggested that it was secreted. OGP was absent in 41/45 normal tissues and positive in oviduct and, weakly, in salivary gland, duodenum and ileum. Forty-six types of non-gynecological tumors were negative, as were gynecological neoplasms except for 2/47 cervical and 3/56 endometrial carcinomas.

Therefore, the inventors have determined that OGP is a new tubal differentiation marker, which characterizes benign and borderline serous neoplasms and may indicate early events in ovarian carcinogenesis.

Accordingly, evaluating OGP levels may be used in the prognostic and diagnostic evaluation of cancers involving OGP, the identification of subjects with a predisposition to such cancers, and in the monitoring of the progress of patients with OGP related cancers.

In an embodiment of the invention, a method is provided for detecting cancer in a patient comprising:
  (a) providing a sample from the patient;
  (b) detecting the level of OGP in the sample; and
  (c) comparing the level of OGP in the sample to a control sample, wherein increased levels of OGP as compared to the control indicates that the patient has cancer.

The term "OGP" as used herein is synonymous with oviduct-specific glycoprotein, oviductin, estrogen-dependent oviductal glycoprotein, or mucin 9 (MUC9). The term OGP includes all of the known OGP molecules including those deposited in GenBank under accession number Q12889 (SEQ ID NO: 1) or those referred to in Arias et al. (Arias EB et al., Biol. Reprod. 51, pages 685-694 (1994)) as well as any isoforms, variants, analogs, derivatives or fragments thereof that are useful in detecting cancer.

The phrase "detecting the level of OGP" includes the detection of the levels of the OGP protein as well as detection of the levels of nucleic acid molecules encoding the OGP protein. Methods for detecting proteins and nucleic acids are discussed in greater detail below.

The term "cancer" as used herein includes all cancers that are associated with increased expression of OGP. In a preferred embodiment, the cancer is a gynecological cancer, including, but not limited to, tubal metaplasia, ovarian serous borderline neoplasms, serous adenocarcinomas, low-grade mucinous neoplasms and endometrial tumors. In a specific embodiment, the gynecological cancer is an ovarian neoplasm, undergoing aberrant Mullerian epithelial differentiation.

The term "sample from a patient" as used herein means any sample containing cancer cells that one wishes to detect including, but not limited to, biological fluids (including blood, serum, ascites), tissue extracts, freshly harvested cells, and lysates of bells which have been incubated in cell cultures. In a preferred embodiment, the sample is gynecological tissue, serum or ascites.

The "patient" can be any mammal, preferably human, suspected of having or having a cancer that is suspected to be associated with OGP. The patient is preferably a female mammal suspected of having or having a gynecological cancer or tumor.

The term "control sample" includes any sample that can be used to establish a base or normal level, and may include tissue samples taken from healthy persons or samples mimicking physiological fluid. Examples of control samples include normal ovarian tissues and sections of normal oviduct.

The method of the invention may be used in the diagnosis and staging of cancer, in particular gynecological cancer. The invention may also be used to monitor the progression of a cancer and to monitor whether a particular treatment is effective or not. In particular, the method can be used to confirm the absence or removal of all tumor tissue following surgery, cancer chemotherapy, and/or radiation therapy. The methods can further be used to monitor cancer chemotherapy and tumor reappearance.

In an embodiment, the invention contemplates a method for monitoring the progression of cancer in a patient, comprising:
  (a) providing a sample from a patient;
  (b) determining the level of OGP expression in the sample;
  (c) repeating steps (a) and (b) at a later point in time and comparing the result of step (b) with the result of step (c) wherein a difference in the level of OGP expression is indicative of the progression of the cancer in the patient.

In particular, increased levels of OGP at the later time point may indicate that the cancer is progressing and that the treatment (if applicable) is not being effective. In contrast, decreased levels of OGP at the later time point may indicate that the cancer is regressing and that the treatment (if applicable) is effective.

In another embodiment of the invention, a method is provided for determining whether or not a cancer is benign in a patient comprising:
  (a) providing a sample from the patient;
  (b) detecting the level of OGP in the sample; and
  (c) comparing the level of OGP in the sample to a control sample, wherein increased levels of OGP as compared to the control indicates that the cancer is benign.

In an embodiment of the invention, a method is provided for distinguishing between noninvasive and invasive gynecological cancers, comprising:
  (a) providing a sample from a patient;
  (b) determining the level of OGP expression in the sample; and
  (c) comparing the level of OGP in the sample to a control sample, wherein increased levels of OGP in the sample from a patient as compared to the control indicates that the cancer is noninvasive.

In another embodiment of the invention, a method is provided for distinguishing between early and late stage adenocarcinomas, comprising:
  (a) providing a sample from a patient;
  (b) detecting the level of OGP in the sample; and
  (c) comparing the level of OGP in the sample to a control sample, wherein increased levels in the sample as compared to the control indicates that the cancer is an early stage adenocarcinoma.

In another embodiment, the invention contemplates a method for determining the potential risk to a patient of developing gynecological neoplasms, comprising:
  (a) providing a sample from the patient;
  (b) detecting the level of OGP in the sample; and
  (c) comparing the level of OGP in the sample to a control sample, wherein increased levels of OGP as compared to the control indicates that the patient is at risk of developing gynecological neoplasms.

A variety of methods can be employed for the above described diagnostic and prognostic evaluation of cancers involving OGP, and the identification of subjects with a predisposition to such disorders. Such methods may rely, for example, on the detection of nucleic acid molecules encoding OGP, and fragments thereof, or the detection of the OGP protein using, for example, antibodies directed against OGP, including peptide fragments. Each of these is described below.

(a) Methods for Detecting Nucleic Acid Molecules

In one embodiment, the methods of the invention involve the detection of nucleic acid molecules encoding OGP. Those skilled in the art can construct nucleotide probes for use in the detection of nucleic acid sequences encoding OGP in samples. Suitable probes include nucleic acid molecules based on nucleic acid sequences encoding at least 5 sequential amino acids from regions of OGP, preferably they comprise 15 to 30 nucleotides. A nucleotide probe may be labeled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode OGP. The nucleotide probes may also be useful in the diagnosis of disorders involving an OGP, in monitoring the progression of such disorders, or in monitoring a therapeutic treatment. In an embodiment, the probes are used in the diagnosis of, and in monitoring the progression of cancer, preferably gynecological cancer.

The probe may be used in hybridization techniques to detect genes that encode OGP proteins. The technique generally involves contacting and incubating nucleic acids (e.g. recombinant DNA molecules, cloned genes) obtained from a sample from a patient or other cellular source with a probe under conditions favorable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules may involve the amplification of specific gene sequences using an amplification method such as polymerase chain reaction (PCR), followed by the analysis of the amplified molecules using techniques known to those skilled in the art. Suitable primers can be routinely designed by one of skill in the art.

Hybridization and amplification techniques described herein may be used to assay qualitative and quantitative aspects of expression of genes encoding OGP. For example, RNA may be isolated from a cell type or tissue known to express a gene encoding OGP, and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively splice transcripts detected in normal individuals relative to those individuals exhibiting symptoms of a cancer involving an OGP protein or gene.

The primers and probes may be used in the above described methods in situ i.e. directly on tissue sections (fixed and/or frozen) of patient tissue obtained from biopsies or resections.

Accordingly, the present invention provides a method of detecting cancer
in a patient comprising:
(a) providing a sample from the patient;
(b) extracting nucleic acid molecules comprising the OGP gene or portion thereof from the sample;
(c) amplifying the extracted nucleic acid molecules using the polymerase chain reaction;
(d) determining the presence of nucleic acid molecules encoding OGP; and
(e) comparing the level of OGP in the sample to a control sample, wherein increased levels of OGP as compared to the control indicates that the patient has cancer.

(b) Methods for Detecting OGP Proteins

In another embodiment, the methods of the invention involve the detection of the OGP protein. In one embodiment, the OGP protein is detected using antibodies that specifically bind to OGP.

Antibodies to OGP may be prepared using techniques known in the art. For example, by using a peptide of OGP, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated.

The term "antibody" as used herein is intended to include fragments thereof which also specifically react with an OGP or fragments thereof. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of OGP antigens of the invention (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, such as, but not limited to, single-chain Fv monoclonal antibodies reactive against OGP may also be generated by screening expression libraries encoding immunoglobulin genes, or portions thereof, expressed in bacteria with peptides produced from the nucleic acid molecules of OGP. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

Antibodies specifically reactive with OGP, or derivatives, such as enzyme conjugates or labeled derivatives, may be used to detect OGP in various samples (e.g. biological materials). They may be used as diagnostic or prognostic reagents and they may be used to detect abnormalities in the level of protein expression, or abnormalities in the structure, and/or temporal, tissue, cellular, or subcellular location of an OGP. In vitro immunoassays may also be used to assess or monitor the efficacy of particular therapies. The antibodies of the invention may also be used in vitro to determine the level of expression of a gene encoding OGP in cells genetically engineered to produce an OGP protein.

The antibodies may be used in any known immunoassays which rely on the binding interaction between an antigenic determinant of OGP and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify OGP in a sample in order to determine its role in cancer and to diagnose the cancer.

In particular, the antibodies of the invention may be used in immuno-histochemical analyses, for example, at the cellular and subcellular level, to detect an OGP protein, to localize it to particular cells and tissues, and to specific subcellular locations, and to quantitate the level of expression.

Cytochemical techniques known in the art for localizing antigens using light and electron microscopy may be used to detect OGP. Generally, an antibody of the invention may be labeled with a detectable substance and an OGP protein may be localised in tissues and cells based upon the presence of the detectable substance. Examples of detectable substances include, but are not limited to, the following: radioisotopes (e.g., $^3H$, $^{14}C$, $^{35}S$, $^{125}I$, $^{131}I$) fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against OGP protein. By way of example, if the antibody having specificity against OGP protein is a rabbit IgG antibody, the second antibody may be goat anti-rabbit gamma-globulin labeled with a detectable substance as described herein.

Where a radioactive label is used as a detectable substance, OGP may be localized by radioautography. The results of radioautography may be quantitated by determining the density of particles in the radioautographs by various optical methods, or by counting the grains.

Labeled antibodies against OGP protein may be used in locating tumor tissue in patients undergoing surgery i.e. in imaging. Typically for in vivo applications, antibodies are labeled with radioactive labels (e.g. iodine-123, iodine-125, iodine-131, gallium-67, technetium-99, and indium-111). Labeled antibody preparations may be administered to a patient intravenously in an appropriate carrier at a time several hours to four days before the tissue is imaged. During this period unbound fractions are cleared from the patient and the only remaining antibodies are those associated with tumor tissue. The presence of the isotope is detected using a suitable gamma camera. The labeled tissue can be correlated with known markers on the patient's body to pinpoint the location of the tumor for the surgeon.

Accordingly, in another embodiment the present invention provides a method for detecting cancer in a patient comprising:

(a) providing a sample from the patient;

(b) contacting the sample with an antibody that binds to OGP;

(c) detecting the level of OGP in the sample; and (d) comparing the level of OGP in the sample to a control sample, wherein increased levels of OGP as compared to the control indicates that the patient has cancer.

The methods of the invention described herein may also be performed using microarrays, such as oligonucleotide arrays, cDNA arrays, genomic DNA arrays, or tissue arrays. Preferably the arrays are tissue microarrays.

In any of the above diagnostic methods, detection or measurement of other cancer markers, in particular markers associated with gynecological cancer such as CA125, may be carried out.

II. Kits

The methods described herein may be performed by utilizing pre-packaged diagnostic kits comprising the necessary reagents to perform any of the methods of the invention. For example, the kits may include at least one specific nucleic acid or antibody described herein, which may be conveniently used, e.g., in clinical settings, to screen and diagnose patients and to screen and identify those individuals exhibiting a predisposition to developing cancer. The kits may also include nucleic acid primers for amplifying nucleic acids encoding OGP in the polymerase chain reaction. The kits can also include nucleotides, enzymes and buffers useful in the method of the invention as well as electrophoretic markers such as a 200 bp ladder. The kit will also include detailed instructions for carrying out the methods of the invention.

The following non-limiting examples are illustrative of the present invention:

EXAMPLES

Example 1

Objective

With neoplastic progression, the precursor of epithelial ovarian cancers, the ovarian surface epithelium (OSE), undergoes Mullerian differentiation, usually of the oviductal type. The aim of this example was to examine the expression of oviduct-specific glycoprotein (OGP), a marker of normal oviductal epithelium, for use as a diagnostic or prognostic marker for ovarian cancer.

In this example, the inventors tested the hypothesis that OGP may also be a marker expressed during the aberrant Mullerian epithelial differentiation of ovarian neoplasms.

Materials and Methods

Tissues and Array Construction.

Archival formalin-fixed paraffin-embedded normal and tumor tissues were collected from the Departments of Pathology of Vancouver Hospital and Health Science Center and Stanford Medical Center. Immunohistochemical staining was performed on whole tissue sections (19 normal ovaries, 14 benign serous cystadenomas) and tissue microarrays (ovarian tumor array, normal tissue array, and multi-tumor tissue array). The ovarian tumor tissue array consisted of 3 benign mucinous cystadenomas, 89 borderline, and 283 malignant ovarian tumors. The multi-tissue and multi-tumor tissue arrays consisted of 433 cases representing 45 normal tissues and 51 benign and malignant tumor types from 37 different tissues. For tissue microarrays, representative normal and tumor regions were identified from hematoxylin and eosin-stained sections. From each specimen duplicate tissue cores with a diameter of 0.6 mm were punched and arrayed on a recipient paraffin block as described previously [Alkushi, A. et al., 2003]. The multitissue microarrays were constructed using a Beecher Instruments Micro Tissue Arrayer. Sections of the completed tissue array blocks were cut at 4 mm and placed on silanized glass slides. These sections were used for immunohistochemical analysis. Sections of normal oviduct (mid- and late-proliferative phase) were used as positive controls [Rapisarda, J. J. et al., 1993].

Immunohistochemistry.

Sections from paraffin-embedded tissues were deparaffinized, rehydrated and treated with 30% $H_2O_2$ for 5 min, and submitted to antigen retrieval by microwave oven treatment for 10 minutes in 10 mM citrate buffer at pH 6.0. Slides were subsequently incubated in normal goat serum for 30 min followed by staining for human OGP using the rabbit anti-HuOGP antibody [Rapisarda, J. J. et al., 1993] at a dilution of 1:1000 overnight at 4° C. Tissues were then incubated with biotinylated anti-rabbit immunoglobulins at 1:200 dilution (Vector Laboratories, Inc.) at room temperature for 1 hour followed by avidin-biotin peroxidase complexes (Vector Laboratories, Inc.) for 1 hour. Diaminobenzidine (Vector Laboratories, Inc.) was used as the chromogen, and hematoxylin (Sigma) as the nuclear counterstain.

Results

Histologic classification (WHO), grade (FIGO), and results of the OGP analysis are given in Tables 1 and 2. The inventors' analysis included 283 malignant ovarian adenocarcinomas of which 50 were positively stained for OGP. Of these 50 tumors, 26 were serous, 9 were mucinous, 10 were endometrioid, 1 was undifferentiated, and 4 were clear cell carcinomas. No staining was observed in seromucinous, transitional cell or Krukenberg carcinomas (1 case each). No reactivity was found in 41 types of normal tissues while the oviduct and the mucus-secreting epithelia of salivary gland, duodenum and ileum reacted weakly with the antibody. In a multitumor tissue array, 46 types of non-gynecological neoplasms were OGP negative. Among gynecological carcinomas, 2/47 (4%) cervical carcinomas and 3/56 (5%) endometrial carcinomas were positive for OGP. Carcinomas of the vulva (0/11) were negative.

OGP was absent in normal OSE. Of the 19 ovaries examined, 7 had 31 inclusion cysts. Staining for OGP was intense in the cells and lumen of 22 epithelial inclusion cysts lined with metaplastic OSE, moderate in 6 inclusion cysts with cuboidal OSE and absent in flat OSE from 3 inclusion cysts. The majority of serous benign cystadenomas (13/14 cases, 93%) and serous borderline tumors (46/65 cases, 71%) (FIG. 1) were OGP positive. Among invasive tumors, only 26 of 184 serous adenocarcinomas stained positively for OGP. These included 5/8 (63%) grade 1, 7/41 (17%) grade 2 and 14/134 (10%) grade 3 serous carcinomas. In addition, OGP was also present in borderline and low-grade mucinous tumors but absent in 3 mucinous cystadenomas. About 25% of the endometrioid borderline and malignant tumors also expressed OGP (Table 1).

Figure 1:
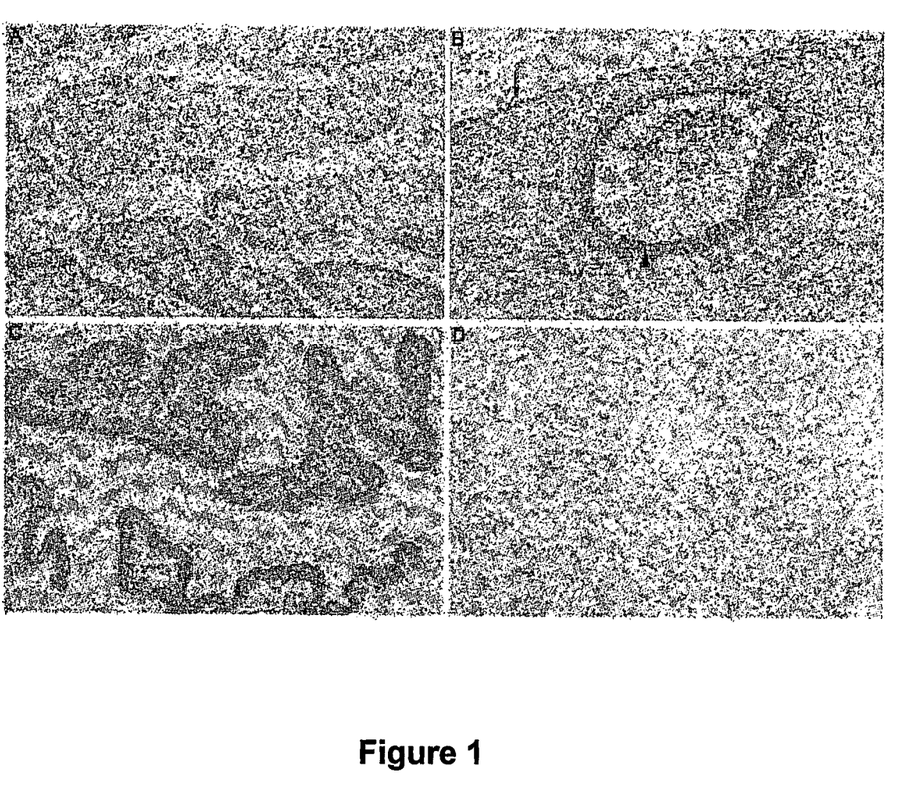
FIG. 1 is series of photographs of tissue sections providing an immunocytochemical demonstration of OGP. (A) Normal oviductal epithelium is positive for OGP. (B) It is absent in normal OSE (arrow) but present in epithelial inclusion cysts (arrowhead) which have undergone tubal metaplasia. Note OGP staining in the lumen of the cyst. (C) OGP in a serous borderline tumor. (D) Invasive serous adenocarcinoma, OGP negative.

In most of the tumors, OGP staining was apical, sometimes with evidence of secretion. All of the epithelial cells were positively stained for OGP in inclusion cysts and serous borderline tumors and in all but one benign serous cystadenoma, while the percentage of positive cells in the carcinoma tissues varied (Table 2). Intense staining was observed in the lumen of epithelial inclusion cysts and benign serous cystadenomas. Connective tissue stroma in both the normal and tumor tissues did not stain (FIG. 1).

Discussion

The tendency for ovarian surface epithelium (OSE) to undergo aberrant Mullerian differentiation during tumorigenesis led the inventors to examine in this example, the expression of a specific differentiation marker for oviductal epithelium, oviduct-specific glycoprotein (OGP), in normal and neoplastic OSE. OGP was absent in normal OSE, present in inclusion cysts and in the majority of benign and borderline serous tumors, but absent in most invasive serous adenocarcinomas. The expression of OGP was almost entirely limited to ovarian neoplasms. This specificity may help to distinguish ovarian tumors from those originating at other sites.

Developmentally, OSE arises from the mesodermal coelomic epithelium, as do the Mullerian duct-derived epithelia of the oviduct, endometrium, and endocervix. However, unlike these latter complex tissues, OSE lacks many of their differentiated epithelial markers [Auersperg, N. et al., 2001]. Possibly the most important differentiation marker discovered to date is CA125, which has clinically proven to be an important diagnostic tool for ovarian cancer [Bast, R. C. Jr. et al., 1998]. In this example, the present inventors have identified another protein, OGP which, like CA125, is a highly glycosylated secreted protein [Verhage, H. G., et al., 1997]. Unlike CA125, OGP expression in Mullerian-duct derived normal epithelia is limited to the oviduct [Arias, E. B. et al., 1994]. The inventors have shown that OGP, like CA125, is absent in OSE but present in metaplastic OSE lining epithelial inclusion cysts which have undergone tubal differentiation, and in the majority of benign cystadenomas and borderline tumors. However, whereas CA125 is present in the majority of ovarian serous carcinomas [Bast, R. C. Jr. et al., 1998], the expression of OGP is rare in these neoplasms.

These results show that the highest proportion (63%) of invasive serous adenocarcinomas that express OGP are grade 1. However, since OGP is also expressed in most epithelial inclusion cysts, which are believed to be the preferential sites for the initiation of malignant transformation [Scully, R. E., 2000; Auersperg, N. et al., 2001], OGP may also represent an early indicator of neoplastic events.

The proportion of benign and borderline serous epithelial tumors that progress to invasive neoplasms is still not defined, but may be quite low [Scully, R. E., 2000; Scully, R. E. et al., 1998; Hu, J. et al., 2002]. Yet, benign and borderline serous tumors adopt a similar phenotype to serous adenocarcinomas in terms of tubal differentiation, suggesting that the common mechanisms which regulate differentiation in all these tumor types diverge from those responsible for the invasive phenotype.

The ectopic expression of OGP in ovarian epithelial tumors further supports the idea that OSE is a developmentally immature epithelium, which has retained the capacity to alter its state of differentiation under physiological and pathological conditions [Auersperg, N. et al., 2001]. OGP is normally a secretory product of the oviduct and is believed to play an important role in early fertilization events within the oviduct via binding to the zona pellucida of oocytes and embryos [Verhage, H. G. et al., 1997; McCauley, T. C. et al., 2003; O'Day-Bowman, M. B. et al., 2002; Staros, A. L., and Killian, G. J., 1998]. The inventors observed that OGP staining was present in the lumen and surface of cysts and glandular structures of ovarian tumors, suggesting that it may also be secreted. In the oviduct, OGP likely increases the viscosity of the luminal fluid, which in turn would stabilize the microenvironment immediately surrounding the gametes and embryo, thereby preventing dispersal of essential nutrients and ions [Buhi, W. C., 2002]. OGP within the complex papillary structure of the normal oviduct and of the serous adenocarcinomas may similarly contribute to a microenvironment where there is an accumulation of growth promoting factors. The lack of OGP in most high-grade ovarian adenocarcinomas raises the possibility that the cells have acquired increased autonomy, and thus no longer require OGP to facilitate their growth.

The results show that OGP occurs in ovarian epithelial lesions, regardless of their potential to progress to invasive neoplasms. Only a small number of grade 1 serous adenocarcinomas have been examined to date, however, a high proportion of these tumors express OGP, and its consistent presence in metaplastic inclusion cysts suggests that this marker may be an indicator of early events in ovarian carcinogenesis.

Example 2

Overview

OGP expression was investigated in cultured OSE cells, serous borderline ovarian tumor cells and ovarian cancer cell lines via RT-PCR using a cDNA probe specific for HuOGP [Arias E B et al., 1994], and Western blot analysis using the Anti-OGP antibody [Rapisarda J J et al., 1993]. As OGP is a secreted protein, the Anti-OGP antibody [Rapisarda J J et al., 1993] was used to assay conditioned media from cultured cells. The serum and ascites fluid from women was collected and tested for the presence of OGP using ELISA and/or RIA.

Materials and Methods

Reagents.

Anti-OGP antibody [Rapisarda J J et al., 1993] was used for detecting OGP protein in tissue sections and the OGP cDNA [Arias E B et al., 1994] was used as a probe in studying the mRNA expression of OGP.

Tissues and Array Construction.

Archival formalin-fixed paraffin-embedded normal and tumor tissues were collected from a clinical database of cases. Representative normal and tumor regions were identified from hematoxylin and eosin-stained sections. From each specimen duplicate tissue cores with a diameter of 0.6 mm were punched and arrayed on a recipient paraffin block. The multitissue microarrays were constructed using a Beecher Instruments Micro Tissue Arrayer. Sections of the completed tissue array blocks were cut at 4 mm and placed on silanized glass slides. These sections were used for immunohistochemical analysis. Normal ovarian tissue sections were also examined for OGP expression. Sections of normal oviduct (mid- and late-proliferative phase) were used as positive controls.

Immunohistochemistry, Western Blot Analysis and ELISA Assay.

Sections from paraffin-embedded tissue were deparaffinized, rehydrated and treated with 30% $H_2O_2$ for 5 min, and submitted to antigen retrieval by microwave oven treatment for 10 minutes in 10 mM citrate buffer at pH 6.0. Slides were subsequently incubated in normal goat serum for 30 min followed by staining using the rabbit anti-OGP antibody [Rapisarda J J et al., 1993] at a dilution of 1:1000 overnight at 4° C. Tissues were then incubated with biotinylated anti-rabbit immunoglobulins at 1:200 dilution (Vector Laboratories, Inc.) at room temperature for 1 hour followed by avidin-biotin peroxidase complexes (Vector Laboratories, Inc.) for 1 hour. Diaminobenzidine (Vector Laboratories, Inc.) was used as the chromogen and hematoxylin (Sigma) as the nuclear counterstain. Sections were then scored according to the following criteria: Intensity (0=negative, 1 to 3=positive), percentage of cells stained positively (<5%, 5 to 50%, >50%, 100%), and localization (apical, cytoplasmic, lumenal). Scoring results were simplified into either negative (score of 0) or positive (score of 1 to 3) categories, and uninterpretable results were eliminated from further consideration. Score results from duplicate cores were consolidated into one score with positive staining always superseding a negative or uninterpretable result.

Discussion

Ovarian cancer, which is the prime cause of death from gynecological malignancies in North American women, is usually diagnosed in late stages because there are no reliable means of early detection. Furthermore, the criteria that are available to define the precise stage and grade of ovarian carcinomas are limited and based mostly on histopathology. Oviduct-specific glycoprotein (OGP) is a secretory product of the normal oviduct. The inventors discovered in a series of tumors that OGP is produced by 75% of noninvasive borderline serous ovarian adenocarcinomas but only by 24% of invasive serous adenocarcinomas, of which 38% were low grade, and 13% were high grade tumors. OGP was also present in low grade, but not in high grade mucinous and endometrioid adenocarcinomas. See Tables 3 and 4. Thus, OGP is a promising diagnostic marker which will help to differentiate noninvasive from invasive and early from late ovarian adenocarcinomas. These distinctions are important in prognosis and treatment planning. In addition, OGP is a secreted protein which will enable its detection in serum as a diagnostic and predictive marker for ovarian cancer.

TABLE 1

OGP expression in benign, borderline and malignant ovarian tumors

| Subtype | Positive/Total | % |
|---|---|---|
| Serous | | |
| Benign | 13/14 | 93 |
| Borderline | 46/65 | 71 |
| Malignant | | |
| Grade 1 | 5/8 | 63 |
| Grade 2 | 7/41 | 17 |
| Grade 3 | 14/134 | 10 |
| Total Malignant | 26/183 | 14 |
| Seromucinous | | |
| Borderline | 3/5 | 60 |
| Malignant | 0/1 | 0 |
| Mucinous | | |
| Benign | 0/3 | 0 |
| Borderline | 7/14 | 50 |
| Malignant | | |
| Grade 1 | 6/9 | 67 |
| Grade 2 | 2/2 | 100 |
| Grade 3 | 1/4 | 25 |
| Total Malignant | 9/15 | 60 |
| Endometrioid | | |
| Borderline | 1/5 | 20 |
| Malignant | | |
| Grade 1 | 3/13 | 31 |
| Grade 2 | 3/16 | 19 |
| Grade 3 | 4/10 | 40 |
| Total Malignant | 10/39 | 26 |
| Undifferentiated | | |
| Malignant | | |
| Grade 2 | 1/2 | 50 |
| Grade 3 | 0/7 | 0 |
| Total Malignant | 1/9 | 11 |
| Clear cell | | |
| Malignant | | |
| Grade 2 | 1/1 | 100 |
| Grade 3 | 3/33 | 9 |
| Total Malignant | 4/34 | 12 |
| Transitional cell | | |
| Malignant | 0/1 | 0 |
| Krukenberg | | |
| Malignant | 0/1 | 0 |

TABLE 2

Characteristics of OGP immunohistochemical staining in ovarian carcinomas

| | Positive/Total | | Localization | | | | Intensity | | | | Percentage of Positive Cells/Case | | | | | |
|---|---|---|---|---|---|---|---|---|---|---|---|---|---|---|---|---|
| Subtype | No. of cases | % | apical | | cytoplasmic | | weak | | strong | | <20% | | 20-80% | | >80% | |
| Serous | | | | | | | | | | | | | | | | |
| Grade 1 | 5/8 | 63 | 4/5 | 80 | 1/5 | 20 | 2/5 | 40 | 3/5 | 60 | 3/5 | 60 | 2/5 | 40 | 0/5 | 0 |
| Grade 2 | 7/41 | 17 | 5/7 | 71 | 2/7 | 29 | 2/7 | 29 | 5/7 | 71 | 1/7 | 14 | 5/7 | 71 | 1/7 | 14 |
| Grade 3 | 14/134 | 10 | 9/14 | 64 | 5/14 | 36 | 5/14 | 36 | 9/14 | 64 | 8/14 | 57 | 6/14 | 43 | 0/14 | 0 |
| Total | 26/183 | 14 | 18/26 | 69 | 8/26 | 31 | 9/26 | 35 | 17/26 | 65 | 12/26 | 46 | 13/26 | 50 | 1/26 | 4 |
| Mucinous | | | | | | | | | | | | | | | | |
| Grade 1 | 6/9 | 67 | 4/6 | 67 | 2/6 | 33 | 1/6 | 17 | 5/6 | 83 | 1/6 | 17 | 2/6 | 33 | 3/6 | 50 |
| Grade 2 | 2/2 | 100 | 2/2 | 100 | 0/2 | 0 | 0/2 | 0 | 2/2 | 100 | 1/2 | 50 | 0/2 | 0 | 1/2 | 50 |
| Grade 3 | 1/4 | 25 | 0/1 | 0 | 1/1 | 100 | 1/1 | 100 | 0/1 | 0 | 0/1 | 0 | 0/1 | 0 | 1/1 | 100 |
| Total | 9/15 | 60 | 6/9 | 67 | 3/9 | 33 | 2/9 | 22 | 7/9 | 78 | 2/9 | 22 | 2/9 | 22 | 4/9 | 56 |

TABLE 2-continued

Characteristics of OGP immunohistochemical staining in ovarian carcinomas

| Subtype | Positive/Total No. of cases | % | Localization | | | | Intensity | | | | Percentage of Positive Cells/Case | | | | | |
|---|---|---|---|---|---|---|---|---|---|---|---|---|---|---|---|---|
| | | | apical | | cytoplasmic | | weak | | strong | | <20% | | 20-80% | | >80% | |
| Endometrioid | | | | | | | | | | | | | | | | |
| Grade 1 | 3/13 | 31 | 3/3 | 100 | 0/3 | 0 | 0/3 | 0 | 3/3 | 100 | 3/3 | 100 | 0/3 | 0 | 0/3 | 0 |
| Grade 2 | 3/16 | 19 | 2/3 | 67 | 1/3 | 33 | 2/3 | 67 | 1/3 | 33 | 1/3 | 33 | 1/3 | 33 | 1/3 | 33 |
| Grade 3 | 4/10 | 40 | 0/4 | 0 | 4/4 | 100 | 4/4 | 100 | 0/4 | 0 | 0/4 | 0 | 0/4 | 0 | 4/4 | 100 |
| Total | 10/39 | 26 | 5/10 | 50 | 5/10 | 50 | 5/10 | 50 | 5/10 | 50 | 4/10 | 40 | 1/10 | 10 | 5/10 | 50 |

TABLE 3

Comparison of HuOGP expression in epithelial ovarian cancers

| Subtype | n (%) |
|---|---|
| SBLT | 9/12 (75%) |
| IMBLT | 1/1 (100%) |
| Serous carcinoma | 12/51 (24%) |
| Endometrioid carcinoma | 3/9 (33%) |
| Mucinous carcinoma | 4/6 (67%) |
| Undifferentiated carcinoma | 1/7 (14%) |

TABLE 4

HuOGP staining classified according to architecture and grade of epithelial ovarian cancer

| Subtype | Architecture n (%) | | | |
|---|---|---|---|---|
| | Glandular | Papillary | Undifferentiated | Total |
| Serous carcinoma | | 5/13 (38%) | 7/37 (19%) | 12/50 (24%) |
| Grade 1 | | 2/3 (67%) | | 2/3 (67%) |
| Grade 2 | | 3/7 (43%) | 2/10 (20%) | 5/17 (29%) |
| Grade 3 | | 0/3 (0%) | 4/27 (15%) | 4/30 (13%) |
| Endometrioid carcinoma | 1/6 (17%) | 1/1 (100%) | 1/2 (50%) | 3/9 (33%) |
| Grade 1 | 1/5 (20%) | 1/1 (100%) | | 2/6 (33%) |
| Grade 2 | 1/1 (100%) | | 1/1 (100%) | 2/2 (100%) |
| Grade 3 | | | 0/1 (0%) | 0/1 (0%) |
| Mucinous | 4/6 (67%) | | | 4/6 (67%) |
| Grade 1 | 3/5 (60%) | | | 3/5 (60%) |
| Grade 2 | 1/1 (100%) | | | 1/1 (100%) |
| Grade 3 | | | | |
| Undifferentiated | | | 1/7 (14%) | 1/7 (14%) |
| Grade 1 | | | | |
| Grade 2 | | | 1/2 (50%) | 1/2 (50%) |
| Grade 3 | | | 0/5 (0%) | 0/5 (0%) |
| Total | 5/12 (42%) | 6/14 (43%) | 9/46 (20%) | 20/71 (28%) |

FULL CITATIONS FOR REFERENCES REFERRED TO IN THE SPECIFICATION

Alkushi A, Irving J. Hsu F. Dupuis B. Liu C L, Rijn M, Gilks C B. Immunoprofile of cervical and endometrial adenocarcinomas using a tissue microarray. Virchows Arch 2003; 442:271-7.

American Cancer Society. Cancer facts and figures 2003. Atlanta, American Cancer Society Inc., 2003.

Arias E B, Verhage H G, Jaffe R C. Complementary deoxyribonucleic acid cloning and molecular characterization of an estrogen-dependent human oviductal glycoprotein. Biol Reprod 1994; 51:685-94.

Auersperg N, Wong A S, Choi K C, Kang S K, Leung P C. Ovarian surface epithelium: biology, endocrinology, and pathology. Endocr Rev 2001; 22:255-88.

Bast R C Jr, Xu F J, Yu Y H, Barnhill S, Zhang Z, Mills G B. CA 125: the past and the future. Int J Biol Markers 1998; 13:179-87.

Boatman D E, Magnoni G E: Identification of a sperm penetration factor in the oviduct of the golden hamster. Biol Reprod 1995; 52:199-207.

Boice M L, McCarthy T J, Mavrogianis P A, Fazlebas A T, Verhage H G. Localization, of oviductal glycoproteins within the zona pellucida and perivitelline space of ovulated ova and early embryos in baboons (Papio anubis). Biol Reprod 1990; 43:340-6.

Buhi W C. Characterization and biological roles of oviduct-specific, oestrogen-dependent glycoprotein. Reproduction 2002; 123: 355-362.

Davies B R, Worsley S D, Ponder B A. Expression of E-cadherin, alpha-catenin and beta-catenin in normal ovarian surface epithelium and epithelial ovarian cancers. Histopathology 1998; 32:69-80.

Hellstrom I, Raycraft J, Hayden-Ledbetter M, Ledbetter J A, Schummer M, McIntosh M, Drescher C, Urban N, Hellstrom K E. The HE4 (WFDC2) protein is a biomarker for ovarian carcinoma. Cancer Res 2003, 63:3695-3700.

Hu J, Khanna V, Jones M M W, Surti U. Genomic imbalances in ovarian borderline serous and mucinous tumors. Cancer Genet Cytogenet 2002; 139:13-23.

Jaffe R C, Arias E B, O'Day-Bowman M B, Donnelly K M, Mavrogianis P A, Verhage H G. Regional distribution and hormonal control of estrogen-dependent oviduct-specific glycoprotein messenger ribonucleic acid in the baboon (Papio anubis). Biol Reprod 1996; 55:421-6.

Jemal A, Murray T, Samuels A, Ghafoor A, Ward E, Thun M J. Cancer statistics, 2003. CA Cancer J Clin 2003; 53:5-26.

Kabawat S E, Bast R C Jr, Bhan A K, Welch W R, Knapp R C, Colvin R B. Tissue distribution of a coelomic-epithelium-related antigen recognized by the monoclonal antibody OC125. Int J Gynecol Pathol 1983; 2:275-85.

Lapensee L, Paquette Y, Bleau G. Allelic polymorphism and chromosomal localization of the human oviductin gene (MUC9). Fertil Steril 1997; 68:702-8.

Leese H J, Tay J I, Reischl J, Downing S J. Formation of Fallopian tubal fluid: role of a neglected epithelium. Reproduction 2001; 121:339-46.

Maines-Bandiera S L, Auersperg N. Increased E-cadherin expression in ovarian surface epithelium: an early step in metaplasia and dysplasia? Int J Gynecol Pathol 1997; 16:250-5.

Mazurek A, Niklinski J, Laudanski T, Pluygers E. Clinical tumor markers in ovarian cancer. Eur J Cancer Prev 1998; 7:23-35.

McCauley T C, Buhi W C, Wu G M, Mao J, Caamano J N, Didion B A, Day B N. Oviduct-specific glycoprotein modulates sperm-zona binding and improves efficiency of porcine fertilization in vitro. Biol Reprod 2003; 69:828-834.

O'Day-Bowman M B, Mavrogianis P A, Fazleabas A T, Verhage H G. A human oviduct-specific glycoprotein: synthesis, secretion, and localization during the menstrual cycle. Microsc Res Tech 1995; 32:57-69.

O'Day-Bowman M B, Mavrogianis P A, Reuter L M, Johnson D E, Fazleabas A T, Verhage H G. Association of oviduct-specific glycoproteins with human and baboon (Papio anubis) ovarian oocytes and enhancement of human sperm binding to human hemizonae following in vitro incubation. Biol Reprod 1996; 54:60-9.

O'Day-Bowman M B, Mavrogianis P A, Minshall R D, Verhage H G. In vivo versus in vitro oviductal glycoprotein (OGP) association with the zona pellucida (ZP) in the hamster and baboon. Mol Reprod Dev 2002; 62:248-256.

Rapisarda, J J, Mavrogianis P A, O'Day-Bowman M B, Fazleabas A T, Verhage H G. Immunological characterization and immunocytochemical localization of an oviduct-specific glycoprotein in the human. J Clin Endocrinol Metab 1993; 76:1483-8.

Schmidt A, Mavrogianis P A, O'Day-Bowman M B, Jaffe R C, Verhage H G. Characterization of antibodies generated against a conserved portion of oviductal glycoprotein (OGP) and endogenous hamster OGP and their ability to decrease sperm binding to the zona pellucida in vitro. Am J Reprod Immunol 1997, 38:377-83.

Scully R E, Young R H, Clement P B. Atlas of tumor pathology, third series, fascicle 23. Tumors of the ovary, maldeveloped gonads, fallopian tube and broad ligament. Washington D.C.: Armed Forces Institute of Pathology; 1998.

Scully R E. Influence of origin of ovarian cancer on efficacy of screening. Lancet 2000; 355:1028-1029.

Staros A L, Killian G J. In vitro association of six oviductal fluid proteins with the bovine zona pellucida. J Reprod Fertil 1998; 112:131-7.

Sundfeldt K, Piontkewitz Y, Ivarsson K, Nilsson O, Hellberg P, Brannstrom M, Janson P O, Enerback S, Hedin L. E-cadherin expression in human epithelial ovarian cancer and normal ovary. Int J Cancer 1997; 74:275-80.

Verhage H G, Fazleabas A T, Mavrogianis P A, O'Day-Bowman M B, Schmidt A, Arias E B, Jaffe R C. Characteristics of an oviductal glycoprotein and its potential role in fertility control. J Reprod Fertil Suppl 1997; 51:217-26.

Verhage H G, Fazleabas A T, Donnelly K. The in vitro synthesis and release of proteins by the human oviduct. Endocrinology 1988; 122:1639-45.

Verhage H G, Mavrogianis P A, O'Day-Bowman M B, Schmidt A, Arias E B, Donnelly K M, Boomsma R A, Thibodeaux J K, Fazleabas A T, Jaffe R C. Characteristics of an oviductal glycoprotein and its potential role in the fertilization process. Biol Reprod 1998; 58:1098-101.

We claim:

1. A method of detecting ovarian or endometrial cancer in a patient comprising:
   (a) providing a sample from the patient;
   (b) determining the level of oviduct specific glycoprotein (OGP) protein having the sequence shown in SEQ ID NO:1 in the sample; and
   (c) comparing the level of OGP protein in the sample to a control sample, wherein increased levels of OGP protein as compared to the control indicates that the patient has ovarian or endometrial cancer, wherein the sample from the patient is gynecological tissue or serum.

2. A method according to claim 1 wherein the cancer is ovarian cancer.

3. A method according to claim 2 wherein the cancer is early stage ovarian adenocarcinoma.

4. A method according to claim 1 wherein the cancer is an ovarian serous borderline neoplasm.

5. A method according to claim 4 wherein the ovarian neoplasm is undergoing Mullerian epithelial differentiation.

6. A method according to claim 1 wherein an antibody is used to determine the levels of the OGP protein.

7. The method according to claim 1 wherein the cancer is benign serous ovarian cancer.

8. The method according to claim 1 wherein the cancer is borderline seromucinous ovarian cancer.

9. The method according to claim 1 wherein the cancer is borderline or malignant mucinous ovarian cancer.

10. The method according to claim 1 wherein the cancer is borderline or malignant endometrioid ovarian cancer.

11. The method according to claim 1 wherein the cancer is a grade 2 malignant undifferentiated ovarian cancer.

12. The method according to claim 1 wherein the cancer is a grade 2 malignant clear cell ovarian cancer.

* * * * *